US00PP22923P2

(12) United States Plant Patent
Dekker

(10) Patent No.: US PP22,923 P2
(45) Date of Patent: Aug. 7, 2012

(54) *CHRYSANTHEMUM* PLANT NAMED 'DEKGRASSLY'

(50) Latin Name: *Chrysanthemum×morifolium*
Varietal Denomination: Dekgrassly

(75) Inventor: Cornelis W. Dekker, Hensbroek (NL)

(73) Assignee: Dekker Breeding B.V., Hensbroek (NL)

( * ) Notice: Subject to any disclaimer, the term of this patent is extended or adjusted under 35 U.S.C. 154(b) by 0 days.

(21) Appl. No.: 12/932,461

(22) Filed: Feb. 25, 2011

(51) Int. Cl.
*A01H 5/00* (2006.01)

(52) U.S. Cl. ..... Plt./287

(58) Field of Classification Search ..... Plt./287
See application file for complete search history.

*Primary Examiner* — Annette Para
(74) *Attorney, Agent, or Firm* — C. A. Whealy

(57) ABSTRACT

A new and distinct cultivar of *Chrysanthemum* plant named 'Dekgrassly', characterized by its pompon type inflorescences with green-colored ray florets; vigorous growth habit; strong and upright flowering stems; short response time; uniform and freely flowering habit; and excellent postproduction longevity.

2 Drawing Sheets

Botanical designation: *Chrysanthemum×morifolium.*
Cultivar denomination: 'DEKGRASSLY'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Dekgrassly'.

The new *Chrysanthemum* plant is a product of a planned breeding program conducted by the Inventor in Hensbroek, The Netherlands. The objective of the breeding program is to create new freely-flowering cut *Chrysanthemum* plants with pompon inflorescences with green-colored ray florets, strong flowering stems, short response time and excellent postproduction longevity.

The new *Chrysanthemum* plant originated from a cross-pollination made by the Inventor in Hensbroek, The Netherlands in February, 2008, of a proprietary selection of *Chrysanthemum×morifolium* identified as code number 51250, not patented, as the female, or seed, parent with a proprietary selection of *Chrysanthemum×morifolium* identified as code number 06.56587.01, not patented. The new *Chrysanthemum* plant was discovered and selected by the Inventor as a single flowering plant from within the progeny of the stated cross-pollination in a controlled greenhouse environment in Hensbroek, The Netherlands in October, 2008.

Asexual reproduction of the new *Chrysanthemum* plant by terminal cuttings in a controlled greenhouse environment in Hensbroek, The Netherlands since November, 2008 has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Dekgrassly'. These characteristics in combination distinguish 'Dekgrassly' as a new and distinct *Chrysanthemum* plant:

1. Pompon type inflorescences with green-colored ray florets.
2. Vigorous growth habit.
3. Strong and upright flowering stems.
4. Short response time.
5. Uniform and freely flowering habit.
6. Excellent postproduction longevity; plants maintain good substance for about 25 days in an interior environment.

Plants of the new *Chrysanthemum* differ from plants of the female parent selection in the following characteristics:

1. Plants of the new *Chrysanthemum* are more vigorous than plants of the female parent selection.
2. Plants of the new *Chrysanthemum* flower about five days earlier than plants of the female parent selection.
3. Plants of the new *Chrysanthemum* and the female parent selection differ in inflorescence form as plants of the female parent selection have single type inflorescences.
4. Ray florets of plants of the new *Chrysanthemum* are darker green in color than ray florets of plants of the female parent selection.

Plants of the new *Chrysanthemum* differ from plants of the male parent selection in the following characteristics:

1. Plants of the new *Chrysanthemum* are more vigorous than plants of the male parent selection.
2. Plants of the new *Chrysanthemum* flower about five days earlier than plants of the male parent selection.
3. Plants of the new *Chrysanthemum* and the male parent selection differ in inflorescence form as plants of the male parent selection have double type inflorescences.
4. Ray florets of plants of the new *Chrysanthemum* are darker green in color than ray florets of plants of the male parent selection.

Plants of the new *Chrysanthemum* can be compared to plants of *Chrysanthemum×morifolium* 'Dekpaddy', disclosed in U.S. Plant Pat. No. 22,145. In side-by-side comparisons conducted in Hensbroek, The Netherlands, plants of the new *Chrysanthemum* differed from plants of 'Dekpaddy' in the following characteristics:

1. Plants of the new *Chrysanthemum* were more vigorous than plants of 'Dekpaddy'.
2. Plants of the new *Chrysanthemum* flowered about five days earlier than plants of 'Dekpaddy'.
3. Plants of the new *Chrysanthemum* and 'Dekpaddy' differed in ray floret color as plants of 'Dekpaddy' had lighter green-colored ray florets.

BRIEF DESCRIPTION OF THE PHOTOGRAPHS

The accompanying colored photographs illustrate the overall appearance of the new *Chrysanthemum* plant showing the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Dekgrassly' grown as a spray-type.

The photograph on the second sheet comprises close-up views of the upper (top of the photograph) and lower surfaces (bottom of the photograph) of typical inflorescences and leaves of 'Dekgrassly'.

DETAILED BOTANICAL DESCRIPTION

The aforementioned photographs and following observations and measurements describe plants grown during the winter in ground beds in a glass-covered greenhouse in Hensbroek, The Netherlands and under commercial cut *Chrysanthemum* cultural practices. Plants were initially given two weeks of long day/short night treatments followed by short day/long night treatments to induce flower initiation and development. During the production of the plants, day temperatures ranged from 18° C. to 25° C., night temperatures ranged from 20° C. to 22° C. and light levels were about 7,000 lux. Plants were eight weeks old when the photographs and the description were taken. In the following description, color references are made to The Royal Horticultural Society Colour Chart, 2007 Edition, except where general terms of ordinary dictionary significance are used.

Botanical classification: *Chrysanthemum×morifolium* 'Dekgrassly'.

Parentage:

*Female, or seed, parent*.—Proprietary selection of *Chrysanthemum×morifolium* identified as code number 51250, not patented.

*Male, or pollen, parent*.—Proprietary selection of *Chrysanthemum×morifolium* identified as code number 06.56587.01, not patented.

Propagation:

*Type*.—Terminal vegetative cuttings.

*Time to initiate roots, summer*.—About four days at 20° C.

*Time to initiate roots, winter*.—About six days at 20° C.

*Time to produce a rooted young plant, summer*.—About 13 days at 20° C.

*Time to produce a rooted young plant, winter*.—About 15 days at 20° C.

*Root description*.—Fine, fibrous; light brown in color.

*Rooting habit*.—Freely branching, medium density.

Plant description:

*Appearance and growth habit*.—Herbaceous pompon type cut flower that is typically grown as a spray-type; vigorous growth habit.

*Flowering stem description*.—Aspect: Erect. Strength: Strong. Length: About 60 cm. Stem diameter: About 4 mm. Spray diameter: About 20 cm. Internode length: About 2 cm to 2.5 cm. Texture: Finely pubescent; longitudinally ridged. Color: Close to 146A.

*Foliage description*.—Arrangement: Alternate; simple. Length: About 6 cm to 12 cm. Width: About 4 cm to 7.5 cm. Apex: Acute. Base: Attenuate. Margin: Palmately lobed, serrate; sinuses parallel to convergent. Texture, upper and lower surfaces: Pubescent, slightly rough; veins prominent on lower surface. Venation pattern: Pinnate, reticulate. Color: Developing leaves, upper surface: Close to 137A. Developing leaves, lower surface: Lighter than 137C. Fully developed leaves, upper surface: Close to 147A; venation, close to 137C to 137D. Fully developed leaves, lower surface: Close to 147B; venation, close to 146C. Petiole: Length: About 1.5 cm to 2.5 cm. Diameter: About 2 mm to 3 mm. Texture, upper and lower surfaces: Slightly rough. Color, upper surface: Close to 137C to 137D. Color, lower surface: Close to 146C.

Inflorescence description:

*Appearance*.—Pompon type inflorescence form with ligulate ray florets and tubular disc florets; inflorescences borne perpendicular to axillary laterals (peduncles); ray and disc florets develop acropetally on a capitulum.

*Fragrance*.—Moderately fragrant.

*Flowering response*.—Under natural conditions, plant flower in the autumn/winter in the Northern Hemisphere; at other times of the year, inflorescence initiation and development can be induced under short day/long night conditions (at least 13.5 hours of darkness); uniform flowering habit and short response time, plants exposed to two weeks of long day/short night conditions after planting followed by photoinductive short day/long night conditions flower about 44 days later when grown as a spray-type.

*Postproduction longevity*.—Excellent postproduction longevity; in an interior environment, inflorescences and foliage will maintain good color and substance for about 25 days; inflorescences persistent.

*Quantity of inflorescences*.—Freely flowering habit; when grown as a spray type, about 20 to 25 inflorescences develop.

*Inflorescence size*.—Diameter: About 2.5 cm. Depth (height): About 2 cm. Disc diameter: About 2.5 mm, inconspicuous. Receptacle height: About 3 mm to 4 mm. Receptacle diameter: About 5 mm. Receptacle color: Close to 145B.

*Inflorescence buds*.—Shape: Flattened spherical. Height: About 2 mm. Diameter: About 4 mm to 5 mm. Color: Close to 137C and 145D.

*Ray florets*.—Length: About 1 cm to 1.3 cm. Width: About 3 mm to 4 mm. Shape: Ligulate. Apex: Rounded. Base: Attenuate. Margin: Entire. Texture, upper and lower surfaces: Smooth, glabrous; satiny. Number per inflorescence: About 250 arranged in about 15 whorls. Aspect: Upright to perpendicular; inner florets incurved and outer florets somewhat twisted and curled. Color: When opening, upper surface: Close to 144B; towards the base, close to N144A. When opening, lower surface: Close to 144C; towards the base, close to N144A. Fully opened, upper surface: Close to 144B. Fully opened, lower surface: Close to N144A.

*Disc florets*.—Shape: Fused tubular, erect and elongated. Apex: Dentate. Length: About 3 mm to 5 mm. Diameter: About 1 mm. Number per inflorescence: Ten or fewer massed at the center of the receptacle. Color, when opening: Apex: Close to 144A. Mid-section: Close to 12A. Base: Close to 145D. Color, fully opened: Not observed.

*Involucral bracts*.—Length: About 5 mm to 7 mm. Width: About 1 mm to 4 mm. Shape: Oval-shaped. Apex: Rounded. Base: Rounded to truncate. Margin: Entire. Texture, upper and lower surfaces: Smooth, glabrous. Number per inflorescence: About 25 arranged in about two to three whorls. Color, upper and lower surfaces: Close to 137A.

*Peduncles*.—Length, terminal peduncle: About 3 cm. Length, fourth peduncle: About 4 cm. Length, seventh peduncle: About 5.5 cm. Diameter: About 2 mm to 3 mm. Strength: Strong. Angle: About 30° from the flowering stem axis. Texture: Pubescent; slightly rough. Color: Close to 146B.

*Reproductive organs*.—Androecium: Not observed. Gynoecium: Not observed.

*Seed/fruit*.—Seed and fruit production have not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Dekgrassly' as illustrated and described.

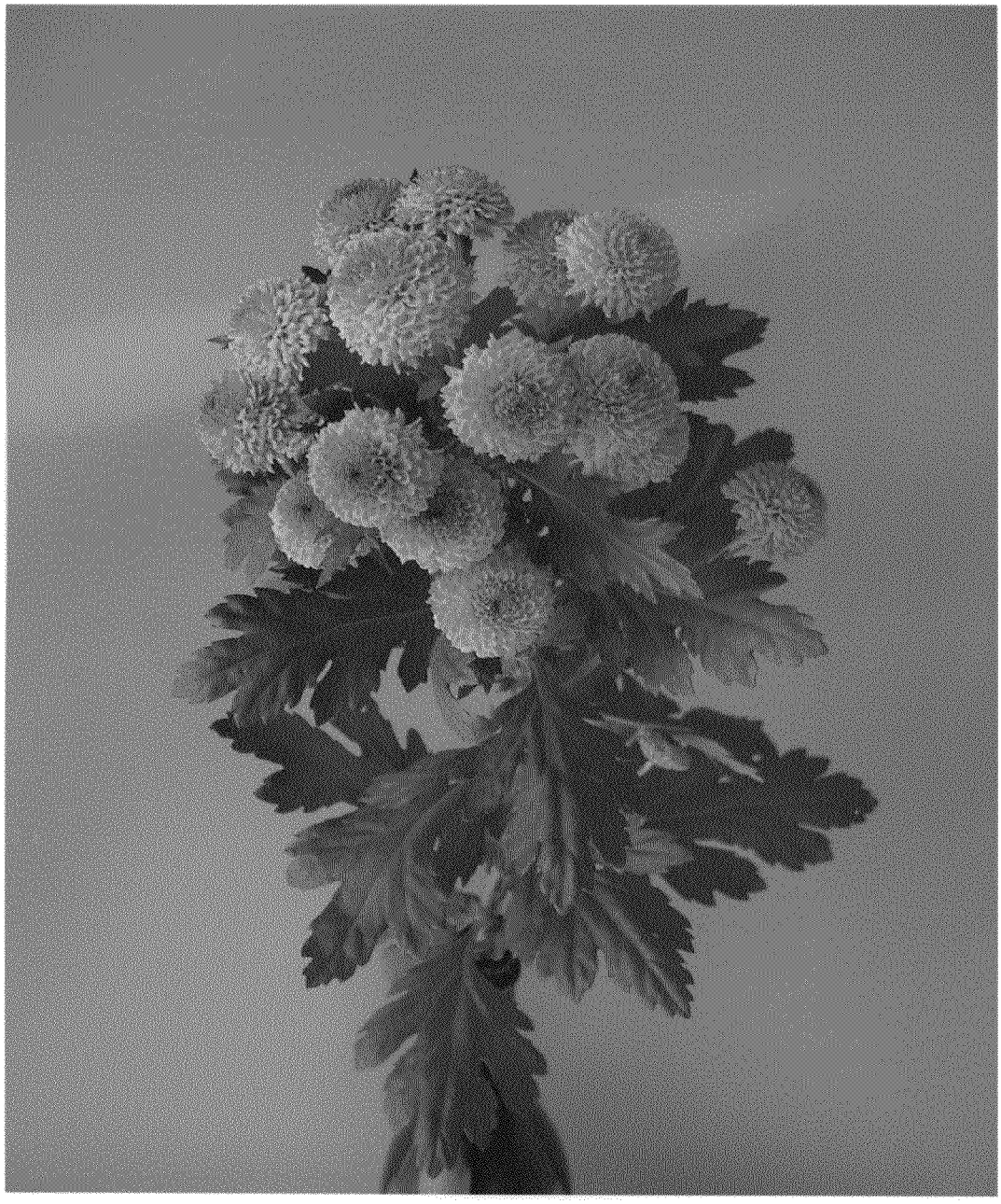

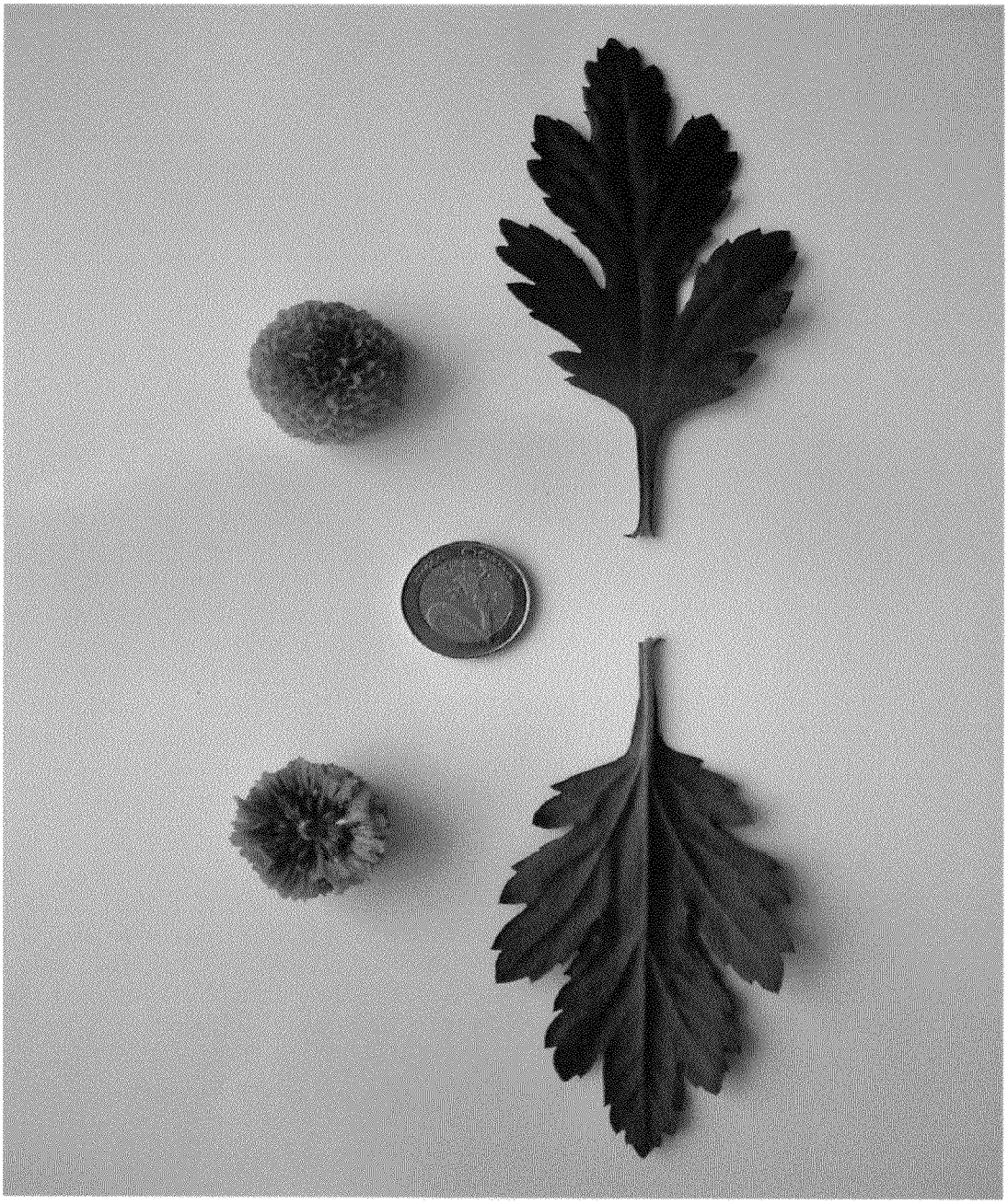

* * * * *